US012778661B2

(12) United States Patent
Allen, IV et al.

(10) Patent No.: US 12,778,661 B2
(45) Date of Patent: Nov. 3, 2026

(54) SYSTEM AND METHOD FOR CUTTING TISSUE USING ELECTROSURGICAL TISSUE SEALING INSTRUMENT

(71) Applicant: Covidien LP, Mansfield, MA (US)

(72) Inventors: James D. Allen, IV, Broomfield, CO (US); William D. Faulkner, Boulder, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/331,742

(22) Filed: May 27, 2021

(65) Prior Publication Data

US 2022/0378490 A1 Dec. 1, 2022

(51) Int. Cl.
*A61B 18/08* (2006.01)
*A61B 18/00* (2006.01)

(52) U.S. Cl.
CPC .. *A61B 18/085* (2013.01); *A61B 2018/00601* (2013.01); *A61B 2018/0063* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS 2,068,721 A 1/1937 Wappler
4,091,813 A 5/1978 Shaw et al.
(Continued)

FOREIGN PATENT DOCUMENTS

EP 1861034 B1 9/2010
EP 2754403 A2 7/2014
(Continued)

OTHER PUBLICATIONS

Gnedenkov et al., "Magnesium fabricated using additive technology: Specificity of corrosion and protection", Journal of Alloys and Compounds, Elsevier, vol. 808, Jul. 29, 2019, XP085792710.
(Continued)

*Primary Examiner* — Joanne M Rodden
*Assistant Examiner* — Nora W Rhodes

(57) ABSTRACT

An electrosurgical device includes jaw members, a thermal cutting element coupled to one of the jaw members. When the jaw members are in an approximated position, power is delivered to the thermal cutting element to maintain the temperature of the thermal cutting element at an operating temperature for cutting sealed tissue grasped between the jaw members. When the jaw members are in the spaced apart position, power is delivered to the thermal cutting element to maintain the temperature of the thermal cutting element at a standby setpoint temperature. In response to a determination of contact between tissue and the thermal cutting element when the jaw members are in the spaced apart position, power is delivered to the thermal cutting element to increase the temperature of the thermal cutting element from the standby setpoint temperature to a cutting setpoint temperature for dissecting tissue.

20 Claims, 9 Drawing Sheets

(52) U.S. Cl.
CPC ............... *A61B 2018/00702* (2013.01); *A61B 2018/00714* (2013.01)

(58) Field of Classification Search
CPC ...... A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | | |
|---|---|---|---|
| 5,389,098 | A | 2/1995 | Tsuruta et al. |
| 5,403,312 | A | 4/1995 | Yates et al. |
| 5,465,895 | A | 11/1995 | Knodel et al. |
| 5,810,811 | A | 9/1998 | Yates et al. |
| 5,827,271 | A | 10/1998 | Buysse et al. |
| 5,833,690 | A | 11/1998 | Yates et al. |
| 5,876,401 | A | 3/1999 | Schulze et al. |
| 5,911,719 | A | 6/1999 | Eggers |
| 6,024,741 | A | 2/2000 | Williamson, IV et al. |
| 6,086,586 | A | 7/2000 | Hooven |
| 6,273,887 | B1 | 8/2001 | Yamauchi et al. |
| 6,402,747 | B1 | 6/2002 | Lindemann et al. |
| 6,602,252 | B2 | 8/2003 | Mollenauer |
| 6,736,813 | B2 | 5/2004 | Yamauchi et al. |
| 6,776,780 | B2 | 8/2004 | Mulier et al. |
| 6,802,843 | B2 | 10/2004 | Truckai et al. |
| 6,808,525 | B2 | 10/2004 | Latterell et al. |
| 6,821,273 | B2 | 11/2004 | Mollenauer |
| 6,860,880 | B2 | 3/2005 | Treat et al. |
| 6,899,710 | B2 | 5/2005 | Hooven |
| 6,929,641 | B2 | 8/2005 | Goble et al. |
| 6,953,461 | B2 | 10/2005 | McClurken et al. |
| 7,011,656 | B2 | 3/2006 | McGaffigan et al. |
| 7,033,356 | B2 | 4/2006 | Atterell et al. |
| 7,070,597 | B2 | 7/2006 | Truckai et al. |
| 7,083,619 | B2 | 8/2006 | Truckai et al. |
| 7,112,201 | B2 | 9/2006 | Truckai et al. |
| 7,125,409 | B2 | 10/2006 | Truckai et al. |
| 7,147,637 | B2 | 12/2006 | Goble |
| 7,169,146 | B2 | 1/2007 | Truckai et al. |
| 7,204,835 | B2 | 4/2007 | Latterell et al. |
| 7,270,664 | B2 | 9/2007 | Johnson et al. |
| 7,276,068 | B2 | 10/2007 | Johnson et al. |
| 7,326,202 | B2 | 2/2008 | McGaffigan |
| 7,329,255 | B2 | 2/2008 | McGaffigan |
| 7,354,440 | B2 | 4/2008 | Truckal et al. |
| 7,357,802 | B2 | 4/2008 | Palanker et al. |
| 7,364,577 | B2 | 4/2008 | Wham et al. |
| 7,396,356 | B2 | 7/2008 | Mollenauer |
| 7,419,490 | B2 | 9/2008 | Falkenstein et al. |
| 7,686,827 | B2 | 3/2010 | Hushka |
| 7,815,641 | B2 | 10/2010 | Dodde et al. |
| 7,931,649 | B2 | 4/2011 | Couture et al. |
| 8,034,051 | B2 | 10/2011 | Martin et al. |
| 8,162,940 | B2 | 4/2012 | Johnson et al. |
| 8,187,273 | B2 | 5/2012 | Kerr et al. |
| 8,197,472 | B2 | 6/2012 | Lau et al. |
| 8,226,649 | B2 | 7/2012 | Falkenstein et al. |
| 8,292,879 | B2 | 10/2012 | Manwaring et al. |
| 8,303,585 | B2 | 11/2012 | Mollenauer |
| 8,372,066 | B2 | 2/2013 | Manwaring et al. |
| 8,377,052 | B2 | 2/2013 | Manwaring et al. |
| 8,394,094 | B2 | 3/2013 | Edwards et al. |
| 8,425,503 | B2 | 4/2013 | Manwaring et al. |
| 8,491,578 | B2 | 7/2013 | Manwaring et al. |
| 8,491,626 | B2 | 7/2013 | Roy et al. |
| 8,523,850 | B2 | 9/2013 | Manwaring et al. |
| 8,523,852 | B2 | 9/2013 | Manwaring et al. |
| 8,551,088 | B2 | 10/2013 | Falkenstein et al. |
| 8,562,598 | B2 | 10/2013 | Falkenstein et al. |
| 8,568,411 | B2 | 10/2013 | Falkenstein et al. |
| 8,597,293 | B2 | 12/2013 | Falkenstein et al. |
| 8,597,297 | B2 | 12/2013 | Couture et al. |
| 8,617,151 | B2 | 12/2013 | Denis et al. |
| 8,623,003 | B2 | 1/2014 | Lau et al. |
| 8,636,730 | B2 | 1/2014 | Keppel |
| 8,734,445 | B2 | 5/2014 | Johnson et al. |
| 8,915,909 | B2 | 12/2014 | Manwaring et al. |
| 8,932,279 | B2 | 1/2015 | Stringham et al. |
| 8,951,248 | B2 | 2/2015 | Messerly et al. |
| 9,005,199 | B2 | 4/2015 | Beckman et al. |
| 9,039,694 | B2 | 5/2015 | Ross et al. |
| 9,050,100 | B2 | 6/2015 | Yates et al. |
| 9,084,606 | B2 | 7/2015 | Greep |
| 9,131,977 | B2 | 9/2015 | Manwaring et al. |
| 9,149,321 | B2 | 10/2015 | Stringham et al. |
| 9,192,427 | B2 | 11/2015 | Johnson et al. |
| 9,265,553 | B2 | 2/2016 | Manwaring et al. |
| 9,265,554 | B2 | 2/2016 | Manwaring et al. |
| 9,265,555 | B2 | 2/2016 | Manwaring et al. |
| 9,265,556 | B2 | 2/2016 | Manwaring et al. |
| 9,320,560 | B2 | 4/2016 | Manwaring et al. |
| 9,387,037 | B2 | 7/2016 | Yang |
| 9,402,679 | B2 | 8/2016 | Ginnebaugh et al. |
| 9,579,146 | B2 | 2/2017 | Johnson et al. |
| 9,918,774 | B2 | 3/2018 | Batchelor et al. |
| 9,931,157 | B2 | 4/2018 | Strobl et al. |
| 9,955,858 | B2 | 5/2018 | Pamnani et al. |
| 10,085,794 | B2 | 10/2018 | Kerr et al. |
| 10,204,773 | B2 | 2/2019 | Sugiyama et al. |
| 10,213,247 | B2 | 2/2019 | Manwaring et al. |
| 2007/0135808 | A1 | 6/2007 | Kupferschmid et al. |
| 2007/0265616 | A1 | 11/2007 | Couture et al. |
| 2008/0058802 | A1* | 3/2008 | Couture ............. A61B 18/1442 606/51 |
| 2008/0086195 | A1 | 4/2008 | Atanasoka et al. |
| 2012/0226270 | A1 | 9/2012 | Manwaring et al. |
| 2013/0282003 | A1* | 10/2013 | Messerly ........... A61B 18/1442 606/169 |
| 2014/0135804 | A1 | 5/2014 | Weisenburgh, II et al. |
| 2015/0374430 | A1* | 12/2015 | Weiler ............... A61B 18/1445 606/46 |
| 2017/0014175 | A1* | 1/2017 | Takashino .......... A61B 18/1445 |
| 2017/0156788 | A1 | 6/2017 | Johnson et al. |
| 2017/0196648 | A1 | 7/2017 | Ward et al. |
| 2017/0245923 | A1* | 8/2017 | Takashino ............ A61B 18/085 |
| 2018/0303322 | A1 | 10/2018 | Pamnani et al. |
| 2019/0000538 | A1 | 1/2019 | Widenhouse et al. |
| 2019/0262062 | A1 | 8/2019 | Akagane |
| 2019/0274717 | A1* | 9/2019 | Nott ............... A61B 17/320092 |
| 2020/0100830 | A1* | 4/2020 | Henderson ........ H04M 1/72406 |
| 2020/0100839 | A1* | 4/2020 | Efremkin ............. A61B 18/245 |

FOREIGN PATENT DOCUMENTS

| | | | |
|---|---|---|---|
| EP | 3222239 | A1 | 9/2017 |
| EP | 3505103 | A1 | 7/2019 |
| EP | 3769709 | A1 | 1/2021 |

OTHER PUBLICATIONS

International Search Report and Written Opinion issued in International Application No. PCT/US2020/061998 mailed Mar. 22, 2021, 14 pages.

Notification of Transmittal of the International Search Report and Written Opinion of the International Searching Authority issued in corresponding application PCT/IB2022/054285 mailed Jul. 26, 2022 (11 pages).

* cited by examiner

| Status | Jaw aperture Sensor | | Jaw force sensor | | Action |
|---|---|---|---|---|---|
| | Jaws approximated | Jaws spaced apart | Jaw force yes | Jaw force no | |
| Movable handle in actuated position, jaw members in approximated position and clamping on tissue disposed in the jaw aperture | x | | x | | Seal then cut |
| Movable handle in unactuated position, jaw members in spaced apart position, and no jaw force | | x | | x | Open jaw dissection |
| Movable handle partially moved toward fixed handle (e.g., between unactuated and actuated positions), no jaw force | x | | | x | Re-grasp alarm |
| Movable handle in actuated position, tissue too thick causing high jaw aperture | | x | x | | Re-grasp alarm |

FIG. 7

SYSTEM AND METHOD FOR CUTTING TISSUE USING ELECTROSURGICAL TISSUE SEALING INSTRUMENT

FIELD

The present disclosure relates to electrosurgical devices and, more particularly, to methods and systems for using an electrosurgical tissue sealing device having a cutting element for cutting tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon severs the treated tissue. Accordingly, many electrosurgical forceps are designed to incorporate a knife that is advanced between the jaw members to cut the treated tissue while the tissue is grasped between the jaw members. As an alternative to a mechanical knife, an energy-based tissue cutting element may be provided to cut the treated tissue using energy, e.g., thermal, electrosurgical, ultrasonic, light, or other suitable energy.

When dissecting tissue, a surgeon typically relies on a second surgical instrument which is substituted or used in conjunction with the sealing instrument to dissect tissue. With certain sealing instruments, the two opposing jaw members may be opened and the jaw member having an energy-based tissue cutting element may be utilized to dissect tissue. Whether utilizing an open jaws tissue dissecting technique or the above-mentioned closed jaws tissue cutting technique, various algorithms may be employed to control the flow of electrical energy to the cutting element to minimize the time it takes for the thermal cutting element and the jaw members to cool down following the procedure so that the risk of unintended damage to surrounding healthy tissue is minimized.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent. Further, to the extent consistent, any or all of the aspects detailed herein may be used in conjunction with any or all of the other aspects detailed herein.

Provided in accordance with aspects of the present disclosure is an electrosurgical device for sealing and cutting tissue. The electrosurgical device includes first and second jaw members each defining a tissue treating surface. The first and second jaw members are pivotably coupled to one another such that at least one of the first or second jaw members is movable relative to the other from a spaced-apart position to an approximated position to grasp tissue between the tissue treating surfaces. The electrosurgical device also includes a thermal cutting element coupled to one of the first or second jaw members and configured to cut tissue. The electrosurgical device also includes a switch configured to control delivery of power to the tissue treating surfaces for sealing tissue grasped between the tissue treating surfaces and to the thermal cutting element for cutting tissue. Activation of the switch when the jaw members are in the approximated position is configured to deliver power to the thermal cutting element to maintain the temperature of the thermal cutting element at an operating temperature for cutting sealed tissue grasped between the tissue treating surfaces. Activation of the switch when the jaw members are in the spaced apart position is configured to cause power to be delivered to the thermal cutting element to warm the thermal cutting element to a standby setpoint temperature and to cause power to be delivered to the thermal cutting element to maintain the temperature of the thermal cutting element at the standby setpoint temperature. Activation of the switch when the jaw members are in the spaced apart position is also configured to cause power to be delivered to the thermal cutting element to increase the temperature of the thermal cutting element from the standby setpoint temperature to a cutting setpoint temperature in response to a determination of contact between tissue and the thermal cutting element. Activation of the switch when the jaw members are in the spaced apart position is also configured to control delivery of power to the thermal cutting element to maintain the temperature of the thermal cutting element at the cutting setpoint temperature to dissect tissue in contact with the thermal cutting element.

In an aspect of the present disclosure, the cutting setpoint temperature is between about 350° C. and about 550° C.

In another aspect of the present disclosure, the standby setpoint temperature is between about 20° C. and about 60° C.

In yet another aspect of the present disclosure, activation of the switch is configured to cause about 50 watts of power to be delivered to the thermal cutting element to warm the thermal cutting element to the standby setpoint temperature.

In still yet another aspect of the present disclosure, the determination of contact between tissue and the thermal cutting element is based on the power delivered to the thermal cutting element to maintain the thermal cutting element at the standby setpoint temperature exceeding a threshold power level.

In another aspect of the present disclosure, activation of the switch is configured to cause power to be delivered to the thermal cutting element to decrease the temperature of the thermal cutting element from the cutting setpoint temperature to the standby setpoint temperature in response to a determination that the thermal cutting element is not in contact with tissue.

In yet another aspect of the present disclosure, determination that the thermal cutting element is not in contact with tissue is based on the power delivered to the thermal cutting element to maintain the thermal cutting element at the cutting setpoint temperature decreasing to a level below a threshold power level.

In still yet another aspect of the present disclosure, completion of cutting of the tissue grasped between the tissue treating surfaces is determined based on a decrease of the power delivered to the thermal cutting element to maintain the temperature of the thermal cutting element at the operating temperature.

According to another embodiment of the present disclosure, an electrosurgical system includes first and second jaw members each defining a tissue treating surface. The first and second jaw members are pivotably coupled to one another such that at least one of the first or second jaw members is movable relative to the other from a spaced-apart position to an approximated position to grasp tissue between the tissue treating surfaces. At least one of the first or second jaw members includes a thermal cutting element configured to cut tissue. The electrosurgical system also includes an electrosurgical generator electrically coupled to the first and second jaw members. The electrosurgical generator is configured to deliver power to the tissue treating surfaces to seal tissue grasped between the tissue treating surfaces when the jaw members are in the approximated position and deliver power to the thermal cutting element to maintain the temperature of the thermal cutting element at an operating temperature for cutting sealed tissue grasped between the tissue treating surfaces when the jaw members are in the approximated position. The electrosurgical generator is also configured to deliver power to the thermal cutting element when the jaw members are in the spaced apart position to warm the thermal cutting element to a standby setpoint temperature and control delivery of power to the thermal cutting element to maintain the temperature of the thermal cutting element at the standby setpoint temperature when the jaw members are in the spaced apart position. The electrosurgical generator is also configured to control delivery of power to the thermal cutting element to increase the temperature of the thermal cutting element from the standby setpoint temperature to a cutting setpoint temperature for dissecting tissue when the jaw members are in the spaced apart position in response to a determination of contact between tissue and the thermal cutting element. The electrosurgical generator is also configured to control delivery of power to the thermal cutting element to maintain the temperature of the thermal cutting element at the cutting setpoint temperature to dissect tissue in contact with the thermal cutting element when the jaw members are in the spaced apart position. The electrosurgical generator is also configured to terminate delivery of power to the thermal cutting element to decrease the temperature of the thermal cutting element.

In an aspect of the present disclosure, the operating temperature of the thermal cutting device for cutting sealed tissue grasped between the tissue treating surfaces is between about 350° C. and about 550° C.

In another aspect of the present disclosure, the cutting setpoint temperature of the thermal cutting device for dissecting tissue when the jaw members are in the spaced apart position is between about 350° C. and about 550° C.

In yet another aspect of the present disclosure, the standby setpoint temperature of the thermal cutting device when the jaw members are in the spaced apart position is between about 20° C. and about 60° C.

In still yet another aspect of the present disclosure, the electrosurgical generator is configured to deliver power to the thermal cutting element when the jaw members are in the spaced apart position to warm the thermal cutting element to the standby setpoint temperature in less than one second.

In another aspect of the present disclosure, the electrosurgical generator is configured to deliver about 50 watts of power to the thermal cutting element to warm the thermal cutting element to the standby setpoint temperature.

In yet another aspect of the present disclosure, the determination of contact between tissue and the thermal cutting element is based on the power delivered to the thermal cutting element to maintain the thermal cutting element at the standby setpoint temperature exceeding a threshold power level.

In still yet another aspect of the present disclosure, the electrosurgical generator is configured to control delivery of power to the thermal cutting element to decrease the temperature of the thermal cutting element from the cutting setpoint temperature to the standby setpoint temperature in response to a determination that the thermal cutting element is not in contact with tissue.

In another aspect of the present disclosure, the determination that the thermal cutting element is not in contact with tissue is based on the power delivered to the thermal cutting element to maintain the thermal cutting element at the cutting setpoint temperature decreasing to a level below a threshold power level.

In yet another aspect of the present disclosure, completion of cutting of the tissue grasped between the tissue treating surfaces is determined based on a decrease of the power delivered to the thermal cutting element to maintain the temperature of the thermal cutting element at the operating temperature.

According to another embodiment of the present disclosure, an electrosurgical system includes first and second jaw members each defining a tissue treating surface. The first and second jaw members are pivotably coupled to one another such that at least one of the first or second jaw members is movable relative to the other from a spaced-apart position to an approximated position to grasp tissue between the tissue treating surfaces. At least one of the first or second jaw members includes a thermal cutting element configured to cut tissue. The electrosurgical system also includes an electrosurgical generator electrically coupled to the first and second jaw members. The electrosurgical generator is configured to deliver power to the tissue treating surfaces to seal tissue grasped between the tissue treating surfaces when the jaw members are in the approximated position. The electrosurgical generator is also configured to deliver power to the thermal cutting element to one of cut sealed tissue grasped between the tissue treating surfaces when the jaw members are in the approximated position or dissect tissue determined to be in contact with the thermal cutting element when the jaw members are in the spaced apart position. The electrosurgical generator is also configured to terminate delivery of power to the thermal cutting element upon detection of completion of the cutting of the sealed tissue when the jaw members are in the approximated position and operate in a low-temperature standby mode to deliver power to the thermal cutting element to maintain the temperature of the thermal cutting element at a standby setpoint temperature between about 20° C. and about 60° C. when the jaw members are in the spaced apart position. The electrosurgical generator is also configured to operate in a high-temperature cut mode to deliver power to the thermal cutting element in response to sensed contact between tissue and the thermal cutting element when the jaw members are in the spaced apart position to increase the temperature of the thermal cutting element from the standby setpoint temperature to a cutting setpoint temperature between about 350° C. and about 550° C. for dissecting tissue. The electrosurgical generator is also configured to control delivery of power to the thermal cutting element during operation in the high-power cut mode to maintain the temperature of the thermal cutting element at the cutting setpoint temperature for dissecting tissue in contact with the thermal cutting element. The electrosurgical generator is also configured to terminate delivery of power to the thermal cutting element to decrease the temperature of the thermal cutting element.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

FIG. 7 is a table illustrating a determined action to be taken based on respective sensor states in accordance with the present disclosure;

DETAILED DESCRIPTION

Figure 1:
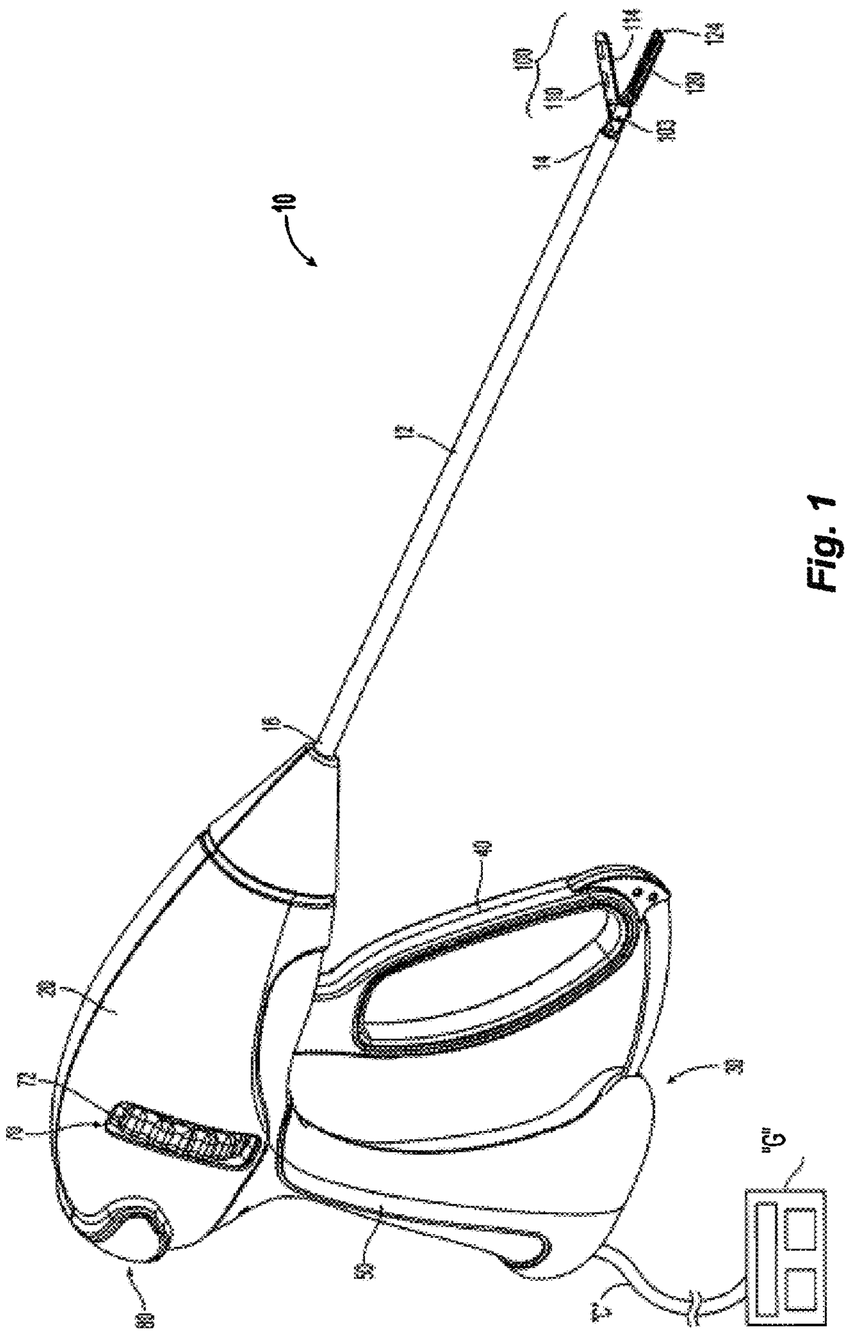
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a rotating assembly 70, an activation switch 80, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue treating surfaces 114, 124 of jaw members 110, 120, respectively, of end effector assembly 100 to provide energy thereto. Activation switch 80 is coupled to tissue treating surfaces 114, 124 and the electrosurgical generator "G" for enabling the selective activation of the supply of energy to jaw members 110, 120 for treating, e.g., cauterizing, coagulating/desiccating, and/or sealing, tissue. Activation switch 80 is also coupled to thermal cutting element 130 of jaw member 120 (FIG. 4) for enabling the selective activation of the supply of energy to thermal cutting element 130 for thermally cutting tissue. In aspects of the present disclosure, forceps 10 may include an additional activation switch (not shown) that serves to activate thermal cutting element 130 independently of activation switch 80 (e.g., activation switch 80 is configured to activate energy delivery to tissue treating surfaces 114, 124 and an additional separate activation switch is configured to activate energy delivery to thermal cutting element 130).

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced apart position and an approximated position to grasp tissue between tissue treating surfaces 114, 124 of jaw members 110, 120. As shown in FIG. 1, movable handle 40 is initially spaced apart from fixed handle 50 in an unactuated position and, correspondingly, jaw members 110, 120 of end effector assembly 100 are disposed in the spaced apart position. Movable handle 40 is movable from the unactuated position towards fixed handle 50 to an actuated position corresponding to the approximated position of jaw members 110, 120. Rotating assembly 70 includes a rotation wheel 72 that is selectively rotatable in either direction to correspondingly rotate shaft 12 and end effector assembly 100 relative to housing 20.

Figure 2:
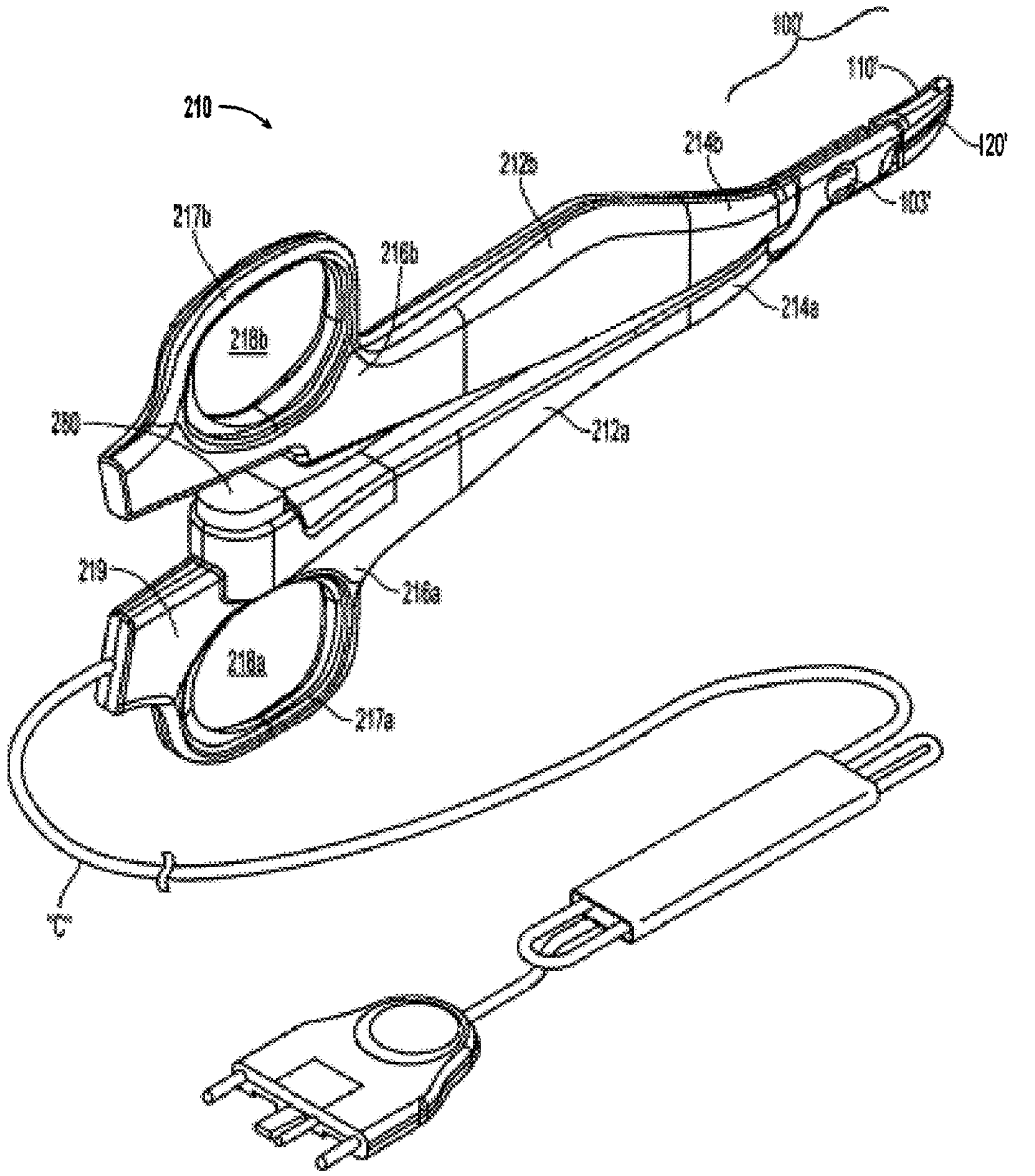
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
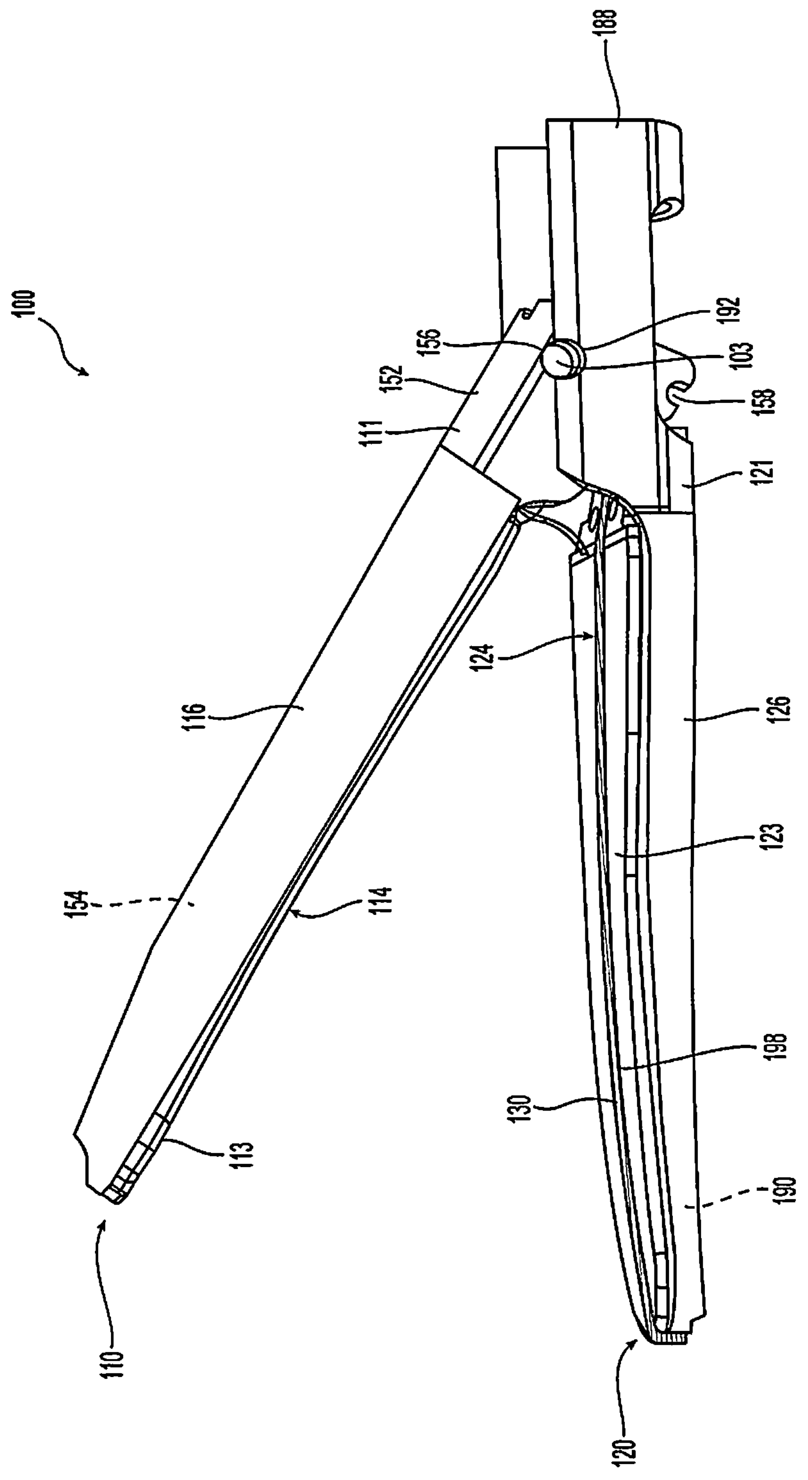
FIG. 4 is a perspective view of an end effector assembly of the forceps of FIG. 1 including first and second jaw members.

Forceps 210 includes two elongated shaft members **212*a*, 212*b*, each having a proximal end portion 216*a*, 216*b*, and a distal end portion 214*a*, 214*b*, respectively. Forceps 210 is configured for use with an end effector assembly 100' similar to and including any of the features of end effector assembly 100 (FIGS. 1 and 4). More specifically, end effector assembly 100' includes first and second jaw members 110', 120' attached to respective distal end portions 214*a*, 214*b* of shaft members 212*a*, 212*b*. Jaw members 110', 120' are pivotably connected about a pivot 103'. Each shaft member 212*a*, 212*b* includes a handle 217*a*, 217*b* disposed at the proximal end portion 216*a*, 216*b* thereof. Each handle 217*a*, 217*b* defines a finger hole 218*a*, 218*b* therethrough for receiving a finger of the user. As can be appreciated, finger holes 218*a*, 218*b* facilitate movement of the shaft members 212*a*, 212*b* relative to one another to, in turn, pivot jaw members 110', 120' from the spaced apart position, wherein jaw members 110', 120' are disposed in spaced relation relative to one another, to the approximated position, wherein jaw members 110', 120'** cooperate to grasp tissue therebetween.

One of the shaft members **212*a*, 212*b* of forceps 210, e.g., shaft member 212*a*, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, an activation switch 280 is provided on one of the shaft members, e.g., shaft member 212*a*, for supplying energy to jaw members 110', 120' to treat tissue upon sufficient approximation of shaft members 212*a*, 212*b*, e.g., upon activation of first activation switch 280 via the other shaft member 212*b*. Activation switch 280 is also coupled to the thermal cutting element (not shown, similar to thermal cutting element 130 of jaw member 120 (FIG. 4)) of one of the jaw members 110', 120' of end effector assembly 100'** and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110', 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
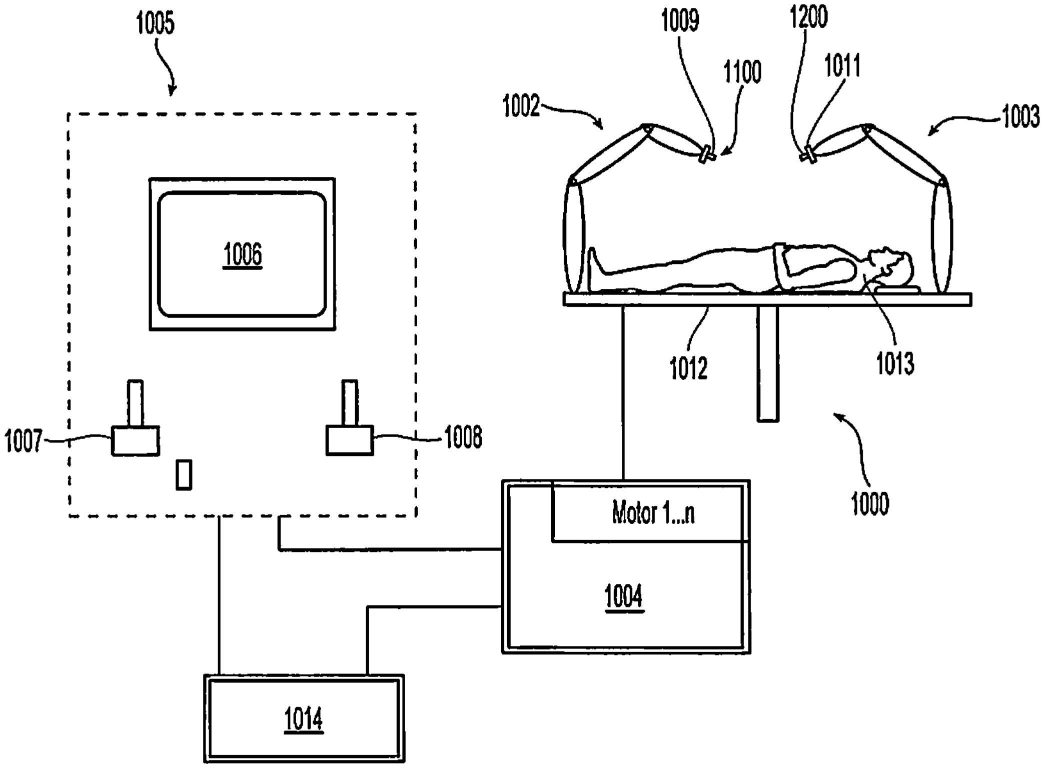
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in an operating mode. Robotic surgical instrument 1000 may be configured for use on a patient 1013 lying on a patient table 1012 to be treated in a minimally invasive manner. Robotic surgical instrument 1000 may further include or be capable of accessing a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to and may include any of the features of end effector assembly 100 (FIGS. 1 and 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Turning to FIG. 4, end effector assembly 100, as noted above, includes first and second jaw members 110, 120. Either or both jaw members 110, 120 may include a structural frame 111, 121, an insulative spacer (not shown), a tissue treating plate 113, 123 defining the respective tissue treating surface 114, 124 thereof, and, in aspects, an outer insulative jacket 116, 126. Tissue treating plates 113, 123 may be pre-formed and engaged with the insulative spacers and/or other portion(s) of jaw members 110, 120 via, for example, overmolding, adhesion, mechanical engagement, etc., or may be deposited onto the insulative spacers, e.g., via sputtering or other suitable deposition technique.

Jaw member 110, as noted above, includes a structural frame 111, an insulative spacer (not shown), a tissue treating plate 113 defining tissue treating surface 114, and, in aspects, an outer insulative jacket 116. Structural frame 111 may be formed from stainless steel or other suitable material configured to provide structural support to jaw member 110. Structural frame 111 includes a proximal flange portion 152 about which jaw member 110 is pivotably coupled to jaw member 120 via pivot 103 and a distal body portion 154 that supports the other components of jaw member 110, e.g., the insulative spacer, tissue treating plate 113, and outer insulative jacket 116 (where provided). In shaft-based or robotic configurations, proximal flange portion 152 enables operable coupling of jaw member 110 to the drive assembly (not shown) to enable pivoting of jaw member 110 relative to jaw member 120 in response to actuation of the drive assembly. More specifically, proximal flange portion 152 may define an aperture 156 for receipt of pivot 103 and at least one catch 158 for receipt of a drive pin of the drive assembly (not shown) such that translation of the drive pin, e.g., in response to actuation of movable handle 40 (FIG. 1) or a robotic drive, pivots jaw member 110 about pivot 103 and relative to jaw member 120 between the spaced apart position and the approximated position. However, other suitable drive arrangements are also contemplated, e.g., using cam pins and cam slots, a screw-drive mechanism, etc. In hemostat-style devices, proximal flange portion 152 is secured to one of the shaft members, e.g., shaft member **212*a* of forceps 210 (see FIG. 2). Proximal flange portion 152** may be bifurcated to define a pair of spaced apart proximal flange portion segments or may otherwise be configured.

Distal body portion 154 of structural frame 111 extends distally from proximal flange portion 152 to support the other components of jaw member 110. The insulative spacer of jaw member 110 is supported on distal body portion 154 of structural frame 111 and is formed from an electrically insulative material capable of withstanding high temperatures such as, for example, up to at least 400° C., although other configurations are also contemplated. The insulative spacer may be formed from ceramic or other suitable material, e.g., PTFE, PEEK, PEI, etc. Tissue treating plate 113 is supported or received on the insulative spacer and is electrically connected, e.g., via one or more electrical leads (not shown), to first activation switch 80 (FIG. 1) and electrosurgical generator "G" (FIG. 1) to enable selective energizing of tissue treating plate 113, e.g., as one pole of a bipolar radio frequency (RF) electrosurgical circuit. However, other suitable energy modalities, e.g., thermal, ultrasonic, light, microwave, infrared, etc., are also contemplated. The insulative spacer serves to electrically isolate structural frame 111 and tissue treating plate 113 from one another.

Continuing with reference to FIG. 4, jaw member 120 includes a structural frame 121, an insulative spacer (not shown), a tissue treating plate 123 defining tissue treating surface 124, and, in aspects, an outer insulative jacket 126. Jaw member 120 further include thermal cutting element 130. Structural frame 121 of jaw member 120 defines a proximal flange portion 188 and a distal body portion 190 extending distally from proximal flange portion 188. Proximal flange portion 188 may be bifurcated to define a pair of spaced apart proximal flange portion segments or may define any other suitable configuration. Proximal flange portion 188 of jaw member 120 and proximal flange portion 152 of jaw member 110 may define a nestled configuration, e.g., wherein one of the proximal flange portions 152, 188 is received within the other, an overlapping configuration, e.g., wherein proximal flange portions 152, 188 at least partially overlap one another, or an offset configuration, e.g., wherein proximal flange portions 152, 188 are positioned in side-by-side relation. Regardless of the particular arrangement of proximal flange portions 152, 188, proximal flange portion 188 further defines a cut out 192 configured for receipt of pivot 103, e.g., welded or otherwise secured therein, to pivotably couple jaw members 110, 120 with one another. Proximal flange portion 188 may be secured to shaft 12 (FIG. 1) in shaft-based configurations (or a corresponding shaft portion in robotic configurations); alternatively, a bilateral configuration may be provided whereby both jaw member 110 and jaw member 120 are pivotable relative to shaft 12 (FIG. 1). In hemostat-style configurations, proximal flange portion 188 may be secured to elongated shaft **212*b* (FIG. 2**).

The insulative spacer of jaw member 120 is supported on distal body portion 190 of structural frame 121 and is formed from an electrically insulative material capable of withstanding high temperatures such as, for example, up to at least 400° C., although other configurations are also contemplated. The insulative spacer may be formed from ceramic or other suitable material, e.g., PTFE, PEEK, PEI. Tissue treating plate 123 is supported or received on the insulative spacer. Tissue treating plate 123, in particular, defines a longitudinally extending slot 198 therethrough along at least a portion of the length thereof. Slot 198 may be transversely centered on tissue treating surface 124 or may be offset relative thereto and may be linear, curved, include angled sections, etc. similarly or differently from the configuration, e.g., curvature, of j aw member 120. Slot 198 exposes a portion of thermal cutting element 130, which may be recessed relative to tissue treating surface 124, substantially co-planar with tissue treating surface 124, or protrude beyond tissue treating surface 124 towards jaw member 110. In aspects where thermal cutting element 130 protrudes, thermal cutting element 130 may contact an opposing portion of jaw member 110 to set a minimum gap distance, e.g., of from about 0.001 inches to about 0.006 inches, between tissue treating surfaces 114, 124 in the approximated position of jaw members 110, 120.

Tissue treating plate 123 is electrically connected, e.g., via one or more electrical leads (not shown), to first activation switch 80 (FIG. 1) and electrosurgical generator "G" (FIG. 1) to enable selective energizing of tissue treating plate 123, e.g., as the other pole of the bipolar (RF) electrosurgical circuit including tissue treating plate 113. In this manner, in the approximated position of jaw members 110, 120 grasping tissue therebetween, bipolar RF electrosurgical energy may be conducted between tissue treating plates 113, 123 and through the grasped tissue to treat, e.g., seal, the grasped tissue. However, other suitable energy modalities, e.g., thermal, ultrasonic, light, microwave, infrared, etc., are also contemplated, as are other suitable tissue treatments, e.g., coagulation.

Thermal cutting element 130 may be secured within and directly to the insulative spacer of jaw member 120 in any suitable manner, e.g., adhesive, friction fitting, overmolding, mechanical engagement, etc., or may be indirectly secured relative to the insulative spacer (in contact with or spaced apart therefrom) via attachment to one or more other components of jaw member 120. Alternatively, the insulative spacer may be omitted and thermal cutting element 130 secured within jaw member 120 (to one or more components thereof) in any other suitable manner. Other suitable configurations for supporting thermal cutting element 130 within jaw member 120 are also contemplated. Thermal cutting element 130 may protrude distally beyond the distal tip of the insulative spacer of jaw member 120 (thus defining the distal-most extent of jaw member 120), may be substantially flush therewith, or may be recessed relative thereto. In aspects where end effector assembly 100, or a portion thereof, is curved, thermal cutting element 130 may similarly be curved.

Figure 5:
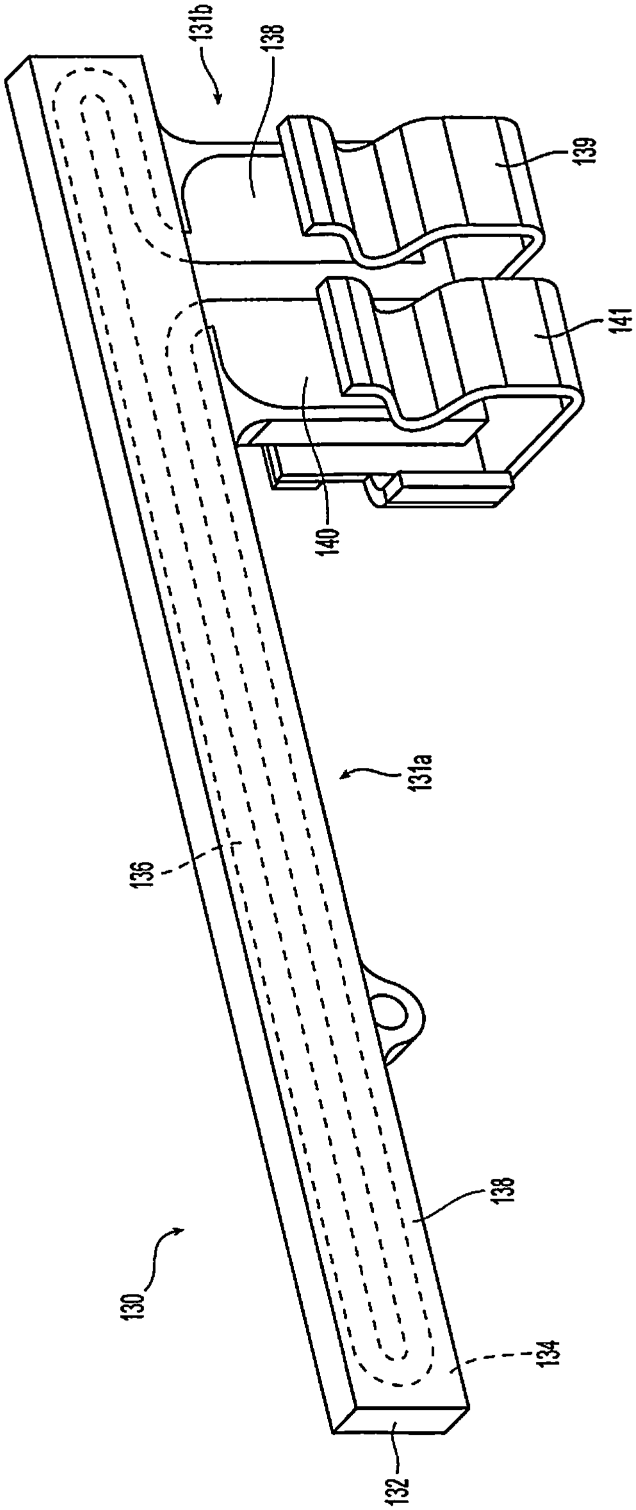
FIG. 5 is a perspective view of the thermal cutting element of the second jaw member of the end effector assembly of FIG. 4.

With additional reference to FIG. 5, thermal cutting element 130 includes a body **131*a* and a proximal extension 131*b*. Thermal cutting element 130 is formed from a base substrate 132 and includes an insulating layer 134 disposed on at least one side of base substrate 132, and a conductive heater trace 136 disposed on insulating layer 134 on at least one side of base substrate 132. Conductive heater trace 136 extends distally along body 131*a* of thermal cutting element 130 and loops back proximally such that first and second ends 138, 140 of conductive heater trace 136 are disposed at proximal extension 131*b* of thermal cutting element 130. First and second contact clips 139, 141 (or other suitable electrical connections) are coupled to proximal extension 131*b* of thermal cutting element 130 in electrical communication with first and second ends 138, 140, respectively, of conductive heater trace 136 for connecting lead wires (not shown) to thermal cutting element 130 to enable application of an AC voltage thereto to heat thermal cutting element 130, e.g., via resistive heating. More specifically, the lead wires electrically connect thermal cutting element 130 to activation switch 80 (FIG. 1) and electrosurgical generator "G" (FIG. 1) to enable selective activation of the supply of an AC voltage to thermal cutting element 130 for heating thermal cutting element 130 to heat and thereby thermally cut tissue. Thermal cutting element 130 may be configured to cut previously (or concurrently) sealed tissue grasped between jaw members 110, 120, tissue extending across jaw member 120, tissue adjacent the distal end of jaw member 120, etc. In addition to or as an alternative to cutting, thermal cutting element 130** may be configured for performing other tissue treatments, e.g., coagulation.

Base substrate 132 may be formed from any suitable material such as, for example, stainless steel, aluminum, aluminum alloys, titanium, titanium alloys, other suitable materials, combinations thereof, etc. Base substrate 132 may be formed via laser cutting, machining, casting, forging, fine-blanking, or any other suitable method. Base substrate 132 may define a thickness of, in aspects, from about 0.003 inches to about 0.030 inches; in other aspects, from about 0.004 inches to about 0.015 inches; and in still other aspects, from about 0.005 inches to about 0.012 inches.

Insulating layer 134, as noted above, may be disposed on either or both sides of base substrate 132. Insulating layer 134 may be a Plasma Electrolytic Oxidation (PEO) coating formed via PEO of either or both sides of base substrate 132. Other suitable materials for insulating layer 134, e.g., PTFE, PEEK, PEI, glass, etc., and/or methods of forming insulating layer 134, e.g., anodization, deposition, spraying, adhesion, mechanical attachment, etc., on either or both sides of base substrate 132 are also contemplated. Where insulating layer 134 is disposed on both sides of base substrate 132, the sides may be of the same or different materials and/or of the same or different thicknesses. Insulating layer 134 may define a thickness (on either or both sides of base substrate 132), in aspects, from about 0.0005 inches to about 0.0015 inches; in other aspects, from about 0.0007 inches to about 0.0013 inches; and in still other aspects, from about 0.0009 inches to about 0.0012 inches. In aspects wherein an insulating base substrate 132, e.g., ceramic, is utilized, insulating layer 134 may be omitted. Further, in aspects, multiple insulating layers 134 are provided on the same side, e.g., two insulating layers 134 on top of one another, each of which may define a thickness (similar or different from one another) within the above-noted ranges or which may collectively define a thickness within the above-noted ranges.

Conductive heater trace 136, as noted above, is disposed on insulating layer 134 (or directly on base substrate 132 where base substrate 132 itself is insulating) on one side of thermal cutting element 130, although it is also contemplated that conductive heater trace 136 extend to the other side of thermal cutting element 130 or that a second conductive heater trace 136 be provided on the other side of thermal cutting element 130. Conductive heater trace 136 may be formed from, for example, platinum, nichrome, kanthal, combinations thereof, or other suitable metal(s) and is disposed on insulating layer 134 via a deposition process, e.g., sputtering, via screen printing, via sintering, or in any other suitable manner. Conductive heater trace 136 may define a thickness, in aspects, from about 0.0002 inches to about 0.0030 inches; in other aspects, from about 0.0006 inches to about 0.002 inches; and in still other aspects, from about 0.0008 inches to about 0.0012 inches.

In aspects, thermal cutting element 130 further includes an encapsulating layer 138 disposed on either or both sides of body 131*a* of thermal cutting element 130 and/or proximal extension 131*b* of thermal cutting element 130. For example, encapsulating layer 138 may encapsulate body 131*a* of thermal cutting element 130 on the side of thermal cutting element 130 including an insulating layer 134 and conductive heater trace 136, although other configurations are also contemplated. Encapsulating layer 138 may define a thickness (on either or both sides of base substrate 132), in aspects, from about 0.0005 inches to about 0.0015 inches; in other aspects, from about 0.0007 inches to about 0.0013 inches; and in still other aspects, from about 0.0009 inches to about 0.0012 inches.

Thermal cutting element 130 as a whole (e.g., including base substrate 132, one or more insulating layers 134 on either or both sides, conductive heater trace 136, and, encapsulating layer 138 on either or both sides) may define a thickness, in aspects, from about 0.010 inches to about 0.018 inches; in other aspects, from about 0.011 inches to about 0.016 inches; and in still other aspects, from about 0.013 inches to about 0.015 inches.

Referring still to FIGS. 4 and 5, thermal cutting element 130 may be configured to receive an applied voltage (VAC), e.g., the voltage output from electrosurgical generator "G" (FIG. 1) to thermal cutting element 130, in aspects, from about 5 volts to about 250 volts; in other aspects, from about 10 volts to about 175 volts; and in still other aspects, from about 25 volts to about 100 volts.

Thermal cutting element 130 may be configured to operate in one or more different modes, e.g., controllable/settable at electrosurgical generator "G" (FIG. 1) or on housing 20 (FIG. 1). More specifically, thermal cutting element 130 may have a single operating mode and corresponding operating temperature for all functions, or may have multiple operating modes each having a corresponding operating temperature for one or more functions such as, for example: back scoring, tenting, plunger cutting, jaws open cutting, jaws closed cutting, slow cutting, fast cutting, spot coagulation, etc. The operating temperatures for the one or more operating modes may be similar or different and any or all may be, in aspects, of at least about 350° C.; in other aspects, from about 350° C. to about 550° C.; in yet other aspects, about or at least 550° C.; in still yet other aspects, from about 400° C. to about 500° C.; and in other aspects, from about 425° C. to about 475° C.

A difference between the resistance of thermal cutting element 130 at room temperature, e.g., about 20° C.-22° C., and an operating temperature, e.g., between about 350° C. and about 550° C., may be, in aspects, from about 5 ohms to about 1500 ohms; in other aspects, from about 10 ohms to about 1000 ohms; and in still other aspects, from about 20 ohms to about 400 ohms.

A Temperature Coefficient of Resistance (TCR) of thermal cutting element 130 may be, in aspects, at least 50 ppm/° C.; in other aspects, at least 900 ppm/° C.; and in still other aspects, at least 3000 ppm/° C.

The power (W) output, e.g., from electrosurgical generator "G" (FIG. 1), to maintain thermal cutting element 130 at the operating temperature of thermal cutting element 130, e.g., from about 350° C. to about 550° C., may be, in aspects, at most 50 W; in other aspects, at most 40 W; and in still other aspects, at most 32 W. The initial power (W) output, e.g., from electrosurgical generator "G" (FIG. 1), to thermal cutting element 130 to reach the operating temperature may be, in aspects, at most 100 W; in other aspects, at most 75 W; and in still other aspects, at most 50 W.

Various different values and ranges for the configuration and operating parameters of thermal cutting element 130 are detailed above. The present disclosure also specifically contemplates any and all combinations of these values and/or ranges as well as any and all ratios and/or ratio ranges of the values and/or ranges of two or more of these operating parameters. For example, appropriate materials, thicknesses, and/or operating parameters may be selected such that, in aspects, thermal cutting element 130 defines a configuration that maximizes the difference between the resistance of thermal cutting element 130 at room temperature and at the operating temperature and, at the same time, minimizes the applied voltage (VAC), all while enabling thermal cutting element 130 to reach a suitable operating temperature.

During a typical sealing and cutting process, the generator "G" cycles through the various algorithms and modes to effectively seal and divide tissue during activation of switch 80. When the jaw members 110, 120 are closed about tissue, the generator "G" can be activated by switch 80 to seal tissue and subsequently activate the thermal cutting element 130 to cut the sealed tissue disposed between the jaw members 110, 120. In aspects of the present disclosure, with jaw members 110, 120 closed about tissue, as long as the surgeon maintains switch 80 in an activated position (e.g., pressed inward toward housing 20), the generator "G" will automatically perform and complete a tissue sealing cycle and subsequently perform and complete a tissue cutting cycle. In certain circumstances, a surgeon may wish to forgo tissue sealing and simply utilize the forceps, e.g., forceps 10, to dissect tissue utilizing thermal cutting element 130 while the jaw members 110, 120 are spaced relative to one another (e.g., jaw members are determined by a position sensor to be in an open position, as discussed in more detail below). In this instance, the generator "G" may bypass the tissue sealing cycle and deliver power to thermal cutting element 130 to perform a tissue cutting cycle when tissue is sensed to be in contact with thermal cutting element 130, as described in more detail below.

When the jaw members 110 and 120 are disposed in an open configuration, it is typically undesirable to allow activation of the tissue contacting surfaces 114, 124 and/or the thermal cutting element 130 and, as a result, in certain circumstances, one or more mechanical or electrical safety mechanisms (not shown) may be employed to avoid unintended activation. Moreover, having one or both of the tissue sealing surfaces 114, 124 or the thermal cutting element 130 activated at the respective power level to seal or cut tissue prior to tissue contact can have unwanted effects. In particular, having switch 80 activated and delivering power to the thermal cutting element 130 for cutting when the thermal cutting element 130 is not in contact with tissue (e.g., prior to tissue contact or subsequent to tissue contact) may unnecessarily increase the temperature of thermal cutting element 130 and one or both of jaw member 110, 120, thereby increasing their cool down times following the conclusion of a procedure. The less time it takes for the temperature of the thermal cutting element 130 and the jaw members 110, 120 to cool down following the conclusion of a procedure, the lower the risk of the thermal cutting element 130 and/or the jaw members 110, 120 causing unintended damage to surrounding healthy tissue.

Figure 6:
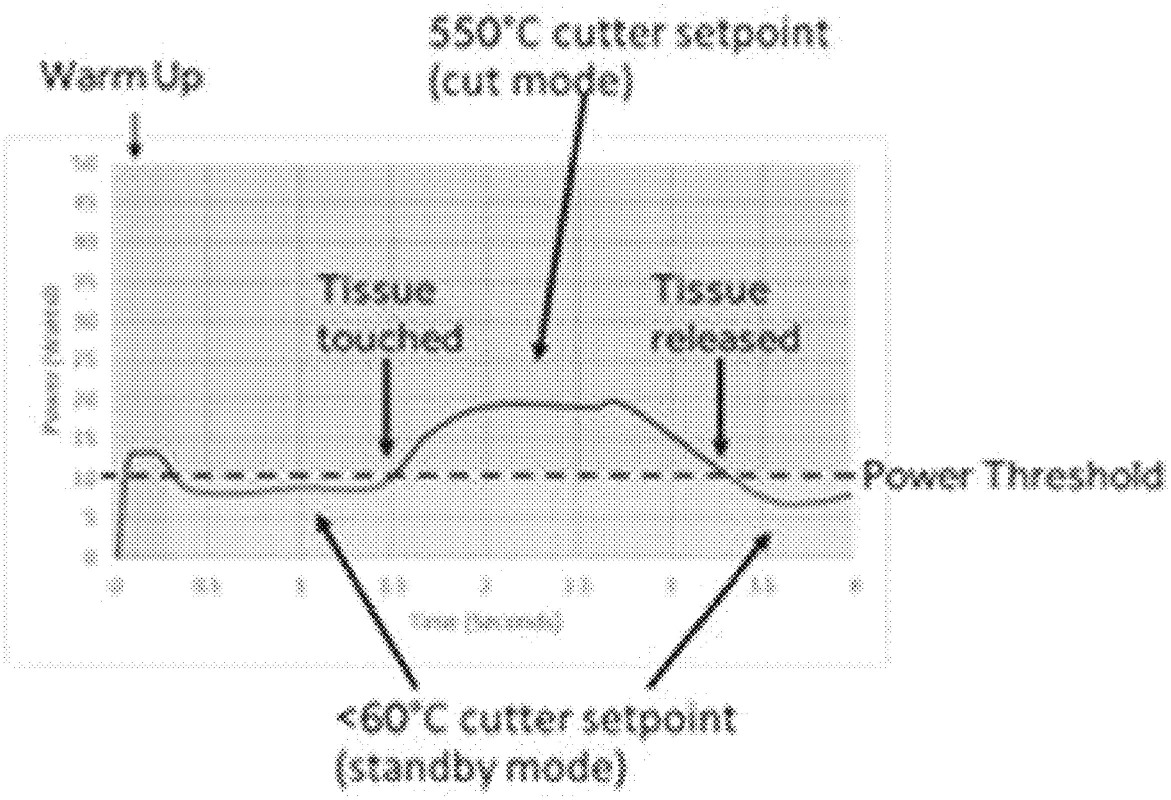
FIG. 6 is an illustrative graph of power delivered to the thermal cutting element as a function of time during an open jaws dissection procedure in accordance with the present disclosure.

FIG. 6 shows a graph of power delivery from the generator "G" to the thermal cutting element 130 over time to illustrate an open jaws dissection during which the generator "G" controls the delivery of power to the thermal cutting element 130 to maintain the temperature of the thermal cutting element 130 at either a low temperature (e.g., between about room temperature and about 60° C.) when thermal cutting element 130 is not in contact with tissue or at a high temperature (e.g., between about 350° C. and about 550° C.) when thermal cutting element 130 is in contact with tissue for dissecting the tissue. More specifically, generator "G" operates in a low-temperature standby mode when thermal cutting element 130 is not in contact with tissue and in a high-temperature cut mode for dissecting tissue when the thermal cutting element 130 is in contact with tissue. The low-temperature standby mode and the high-temperature cut mode are energy delivery algorithms incorporated into generator "G" for delivering electrosurgical energy to one or more of the above-identified surgical forceps 10, 210 to maintain the thermal cutting element 130 at a standby setpoint temperature (e.g., between about room temperature and about 60° C.) when in the low-temperature standby mode or at a cutting setpoint temperature (e.g., between about 350° C. and about 550° C.) when in the high-temperature cut mode. When operating in the low-temperature standby mode, the power delivery from generator "G" to thermal cutting element 130 is initially ramped up (e.g., to about 50 watts) such that the thermal cutting element 130 goes through a warm-up period (e.g., less than one second) during which the temperature of the thermal cutting element 130 is quickly increased to the standby setpoint temperature. Once the thermal cutting element 130 has reached the standby setpoint temperature, the generator "G" reduces power delivery to the thermal cutting element 130 and maintains the thermal cutting element 130 temperature at the standby setpoint temperature. In aspects of the present disclosure, the generator "G" may vary power output to the thermal cutting element, if necessary, to maintain the thermal cutting element 130 at the standby setpoint temperature. The generator "G" operates in the low-temperature standby mode until either switch 80 is deactivated to terminate power delivery to the thermal cutting element 130 or the level of power output of generator "G" required to maintain the temperature of the thermal cutting element 130 at the standby setpoint temperature tissue exceeds a threshold power level (e.g., 0.5 watts, 10 watts, 20 watts, etc.). If the threshold power level is exceeded, the thermal cutting element 130 is determined to be in contact with tissue and the generator "G" switches to operating in the high-temperature cut mode, as described in more detail below. In aspects of the present disclosure, the threshold power level may be based on the size and/or a known thermal profile of the thermal cutting element 130. The thermal profile of the thermal cutting element 130 may include parameters such as, for example, power consumption when contacting tissue, power consumption when not contacting tissue, etc. In aspects of the present disclosure, the thermal profile of the thermal cutting element 130 may be included as part of a thermal profile of jaw member 120. As long as the power consumption of the thermal cutting element 130 during operation in the low-temperature standby mode matches the known power consumption for the thermal cutting element 130 (and/or jaw member 120), it is determined that the thermal cutting element 130 is not in contact with tissue and the generator "G" continues to operate in the low-temperature standby mode. If the power consumption of the thermal cutting element 130 exceeds the known power consumption for the thermal cutting element 130 when not in contact with tissue, it is determined that the thermal tissue cutting element 130 is in contact with tissue since the contacted tissue increases the consumption of the generator "G" output, thereby increasing the power output of the generator "G" required to maintain the thermal cutting element 130 at the standby setpoint temperature. In this manner, the known power consumption of the thermal cutting element 130 may, in aspects, serve as the threshold power level. Upon determining that the thermal cutting element 130 is in contact with tissue, generator "G" switches from operating in low-temperature standby mode to operating in the high-temperature cut mode. In aspects of the present disclosure, sensing tissue contact with the thermal cutting element 130 may be accomplished through various known electrical, mechanical or electro-mechanical circuits and/or mechanisms, e.g., impedance, resistance, optics, sensors, etc.

The generator "G" only operates in high-temperature cut mode if tissue is determined to be in contact with the thermal cutting element 130. When operating in the high-temperature cut mode, power delivery from generator "G" to thermal cutting element 130 is varied as needed to maintain thermal cutting element 130 at the cutting setpoint temperature. In aspects, the power output of the generator "G" required to maintain the thermal cutting element 130 at the cutting setpoint temperature may be based on the size and/or the known thermal profile of the thermal cutting element 130 and/or jaw member 120. The generator "G" operates in the high-temperature cut mode to dissect tissue in contact with the thermal cutting element 130 until either switch 80 is deactivated or the level of power output of generator "G" required to maintain the temperature of the thermal cutting element 130 at the cutting setpoint temperature tissue falls below a threshold power level (e.g., 0.5 watts, 10 watts, 20 watts, etc.). If the power output of generator "G" falls below the threshold power level, it is determined that the thermal cutting element 130 is not in contact with tissue and the generator "G" returns to operating in the low-temperature standby mode. As described above, the threshold power level may, in aspects, be based on the size and/or the known thermal profile of the thermal cutting element 130. If the power consumption of the thermal cutting element 130 during operation in the high-temperature cut mode matches the known power consumption for the thermal cutting element 130 (and/or jaw member 120), it is determined that the thermal cutting element 130 is not in contact with tissue and the generator "G" may return to operating in the low-temperature standby mode if the switch 80 remains activated. Otherwise, switch 80 may be deactivated to terminate power delivery to the thermal cutting element 130, at which point the cool down of the thermal cutting element 130 is initiated such that the temperature of the thermal cutting element 130 decreases over time.

Various electrical and/or mechanical sensing mechanisms in the generator "G", switch 80, or jaw members 110, 120 may be utilized to determine if jaw members 110, 120 are in the spaced apart position or the approximated position, as described below with respect to FIG. 7. If the jaw members 110, 120 are determined to be in the spaced apart position, the generator "G" operates in the low-temperature standby mode. If the jaw members 110, 120 are determined to be in the approximated position and clamping on tissue between tissue sealing surfaces 114, 124, the sealing and cutting cycles may be initiated (as described above) upon activation of switch 80. It is advantageous to detect completion of a tissue cutting cycle so that power delivery from the generator "G" to the thermal cutting element 130 can be immediately terminated to allow the thermal cutting element 130 to begin its cool-down process as quickly as possible following completion of the tissue cutting cycle. As indicated hereinabove, the less time it takes for the temperature of the thermal cutting element 130 and the jaw members 110, 120 to cool down following the conclusion of a procedure, the lower the risk of the thermal cutting element 130 and/or the jaw members 110, 120 causing unintended damage to surrounding healthy tissue. In aspects of the present disclosure, completion of the cutting cycle while jaw members 110, 120 are in the approximated position and clamped on tissue may be detected by one or more algorithms implemented by the generator "G". For example, with the jaw members 110, 120 in the approximated position and clamping tissue, the generator "G" initially ramps up power delivery to the thermal cutting element 130 such that the temperature of the thermal cutting element 130 is quickly (e.g., less than 1 second) increased to a cutting setpoint temperature for cutting the clamped tissue. For example, the generator "G" may initially ramp up power delivery to the thermal cutting element 130 to a level (e.g., about 50 watts) sufficient to quickly increase the temperature of the thermal cutting element 130 to a cutting setpoint temperature (e.g., between about 350° C. and about 550° C.) suitable for cutting tissue clamped between the tissue treating surfaces 114, 124. Once the cutting setpoint temperature is reached, the generator "G" outputs power to the thermal cutting element 130 at a level sufficient to maintain the thermal cutting element 130 at the cutting setpoint temperature. Once the tissue clamped between the tissue treating surfaces 114, 124 is cut, the power output of the generator "G" required to maintain the thermal cutting element 130 at its cutting setpoint temperature decreases by an amount sufficient to indicate completion of the tissue cutting cycle. For example, completion of the tissue cutting cycle may be determined based on the required power output falling below a pre-determined power threshold value and/or the required power output decreasing at a rate of change that exceeds a pre-determined rate of change threshold. Upon completion of the tissue cutting cycle, the generator "G" terminates delivery of power to the thermal cutting element 130. The generator "G" may alert the clinician (e.g., audibly, visually, and/or haptically) that the tissue cutting cycle is complete. Termination of power delivery to the thermal cutting element 130 initiates the cool-down period of the thermal cutting element 130 such that the temperature of the thermal cutting element 130 decreases over time.

Referring now to FIG. 7, and as indicated above, various electrical and/or mechanical sensing mechanisms in generator "G", switch 80, or jaw members 110, 120 may be utilized to determine if jaw members 110, 120 are in the spaced apart position or the approximated position. In this manner, a determination may be made by generator "G" and/or the clinician whether an open jaws tissue dissection algorithm should be implemented by the generator "G", a closed jaws tissue sealing/cutting algorithm should be implemented by the generator "G", or an alert (e.g., audibly, visually, and/or haptically) should be issued by generator "G" that tissue should be re-grasped between the tissue treating surfaces 114, 124. For example, one or more position sensors (not shown) may be positioned in or on surgical forceps 10, 210 to determine a jaw aperture (e.g., a distance between the jaw members 110, 120), a jaw(s) position (e.g., jaws open or jaws closed), and/or the position of movable handle 40 (e.g., unactuated or actuated). The position sensor(s) may sense the position and/or angle of components of forceps 10, 210 that correlate to the jaw aperture (e.g., a closure tube, a push rod, or jaw flags) to determine the jaw aperture. The position sensor(s) may also provide feedback (e.g., audibly, visually, and/or haptically) to a clinician when the jaw aperture between the jaw members 110, 120 is in an acceptable range suitable for sealing tissue between the jaw members 110, 120 (e.g., from about 0.001 inches to about 0.006 inches). In addition, the position sensor(s) may be in communication with the generator "G" to prevent delivery of electrosurgical energy when the gap distance is outside an acceptable range. Additionally, one or more jaw force sensors (not shown) may be positioned in or on surgical forceps 10, 210 to determine a closure force of the jaw members 110, 120 exerted on tissue positioned within the jaw aperture between the jaw members 110, 120. In aspects, the closure force of jaw members 110, 120 may be determined, for example, based on a measured difference between a position of movable handle 40 and a position of the jaw members 110, 120. In some embodiments, the position sensor(s) and/or the jaw force sensor(s) may be a binary sensor having only two states. For example, the position sensor(s) may have either a "jaws spaced apart" or a "jaws approximated" return value indicative of the position of the jaw members 110, 120 and the jaw force sensor(s) may have either a "jaw force yes" or a "jaw force no" return value indicative of whether or not a jaw force is being exerted on the jaw members 110, 120. In this manner, depending on the type of procedure a clinician wishes to perform (e.g., a closed jaws tissue sealing/cutting procedure or an open jaws tissue dissection procedure), a determination may be made by the clinician as to what action can be taken based on the state of the position sensor(s) and the state of the jaw force sensor(s). It is contemplated by this disclosure that the respective states of the position sensor(s) and the jaw force sensor(s) may be considered in combination, as illustrated in FIG. 7, or individually to determine an action to be taken and/or a status of a device (e.g., surgical forceps 10, 210).

FIG. 7 shows a table illustrating various actions that may be taken based on the respective states of the position sensor and the jaw force sensor. When the movable handle 40 is in the actuated position and jaw members 110, 120 are in the approximated position and clamping on tissue disposed between the jaw members 110, 120, the jaw aperture sensor returns a state of "jaws approximated" and the jaw force sensor returns a state of "jaw force yes" indicating that the generator "G" can be activated by switch 80 to seal the clamped tissue and, subsequently, deliver power to the thermal cutting element 130 to cut the sealed tissue. When the movable handle 40 is in the unactuated position and the jaw members 110, 120 are in the spaced apart position, the jaw aperture sensor returns a state of "jaws spaced apart" and the jaw force sensor returns a state of "jaw force no" indicating that the generator "G" can be activated to deliver power to the thermal cutting element 130 for an open jaws tissue dissection procedure. When the movable handle 40 is partially moved from the unactuated position toward the actuated position such that the jaw members 110, 120 are in the approximated position or close to the approximated position and yet no jaw force is sensed, the jaw aperture sensor returns a state of "jaws approximated" and the jaw force sensor returns a state of "jaw force no" indicating that either tissue is improperly grasped between the jaw members 110, 120 or there is an inadequate amount of tissue disposed in the jaw aperture to exert a detectable force on jaw members 110, 120. In this instance, generator "G" may generate a re-grasp alarm to prompt the clinician to re-grasp tissue between jaw members 110, 120. When movable handle 40 is in the actuated position but tissue in the jaw aperture is too thick for jaw members 110, 120 to move to the approximated position, the jaw aperture sensor returns a state of "jaws spaced apart" and the jaw force sensor returns a state of "jaw force yes" indicating that the tissue disposed within the jaw aperture is too thick to be effectively sealed. In this instance, generator "G" and/or the surgical device (e.g., surgical forceps 10, 210) may generate a re-grasp alarm (e.g., audibly, visually, and/or haptically) to prompt the clinician to re-grasp tissue between the jaw members 110, 120.

Figure 8:
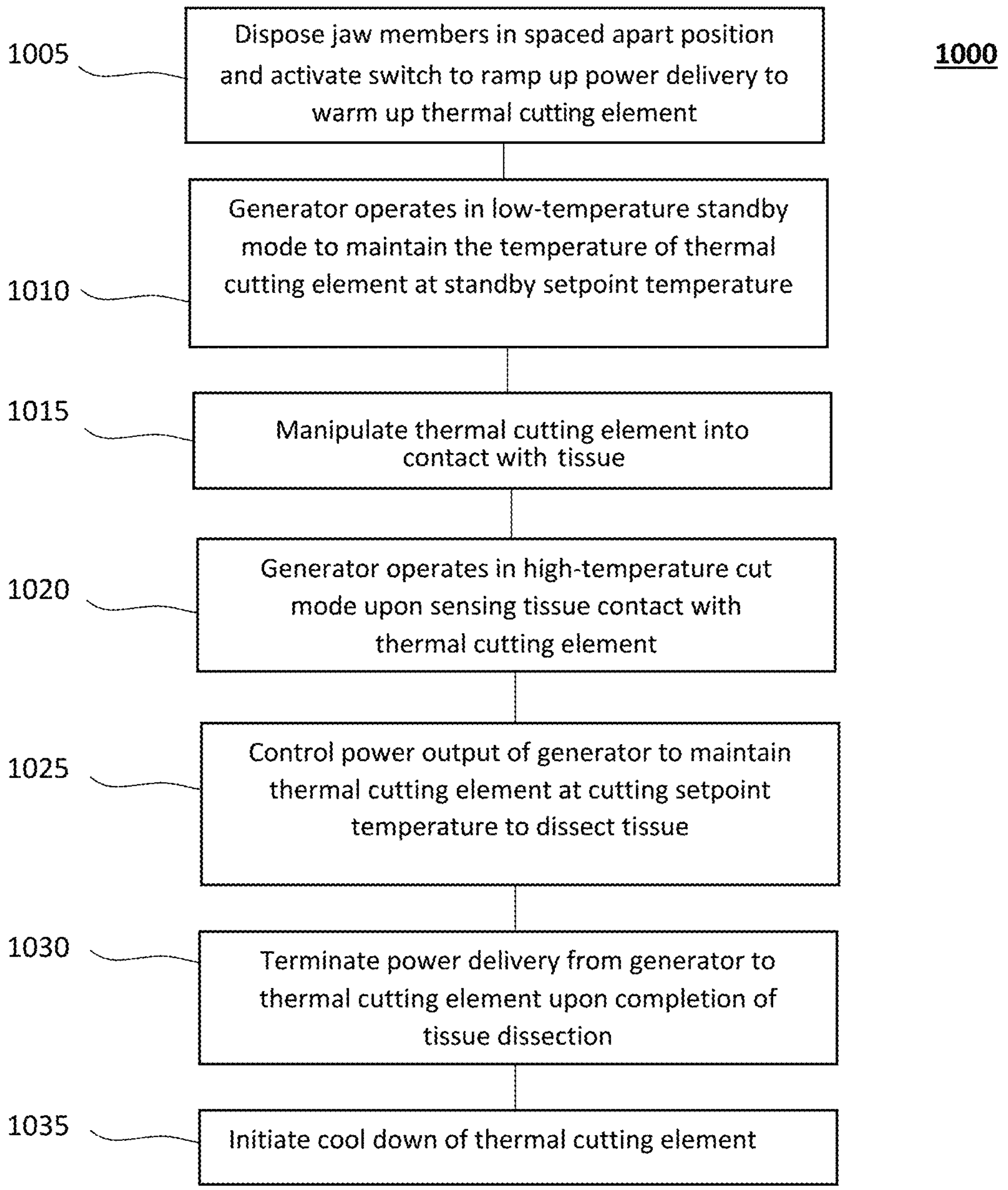
FIG. 8 is a flow chart showing a method for performing an open jaws tissue dissection procedure in accordance with the present disclosure.

FIG. 8 is a flow chart showing the various steps associated with a method 1000 for performing an open jaws tissue dissection procedure in accordance with the embodiment described with respect to FIG. 6. As an initial step 1005, the jaw members, e.g., jaw members 110, 120, are disposed in the spaced apart position and switch 80 is activated to ramp up power delivery from the generator "G" to the thermal cutting element 130 such that the thermal cutting element 130 undergoes a warm-up period (as discussed above). As described above with respect to FIG. 7, a determination that the jaw members 110, 120 are in the spaced apart position may be determined based on the state of one or both of a jaw aperture sensor and a jaw force sensor. In step 1010, the generator "G" operates in the low-temperature standby mode to regulate power delivery to the thermal cutting element 130 and maintain the thermal cutting element 130 temperature at the standby setpoint temperature (e.g., between about room temperature and about 60° C.), as described above. In step 1015, the thermal cutting element 130 is manipulated into contact with tissue for dissection. In step 1020, upon determining tissue contact as described above, the generator "G" operates in the high-temperature cut mode and power delivery is ramped up to increase the temperature of the thermal cutting element 130 to a cutting setpoint temperature (e.g., between about 350° C. and about 550° C.) suitable for tissue dissection. In step 1025, generator "G" controls power delivery to the thermal cutting element 130 while operating in high-temperature cut mode to maintain the thermal cutting element 130 temperature at the cutting setpoint temperature for tissue dissection. In step 1030, upon completion of tissue dissection, power delivery to the thermal cutting element 130 is terminated either automatically by generator "G" or via the clinician deactivating (e.g., releasing) switch 80. In step 1035, the cool down of thermal cutting element 130 is initiated upon termination of power delivery to thermal cutting element 130 and the temperature of thermal cutting element 130 and/or jaw members 110, 120 decreases over time. In aspects of the present disclosure, upon completion of tissue dissection in step 1030, the generator "G" may return to operating in low-temperature standby mode while switch 80 is activated if tissue is not determined to be in contact with the thermal cutting element 130.

Figure 9:
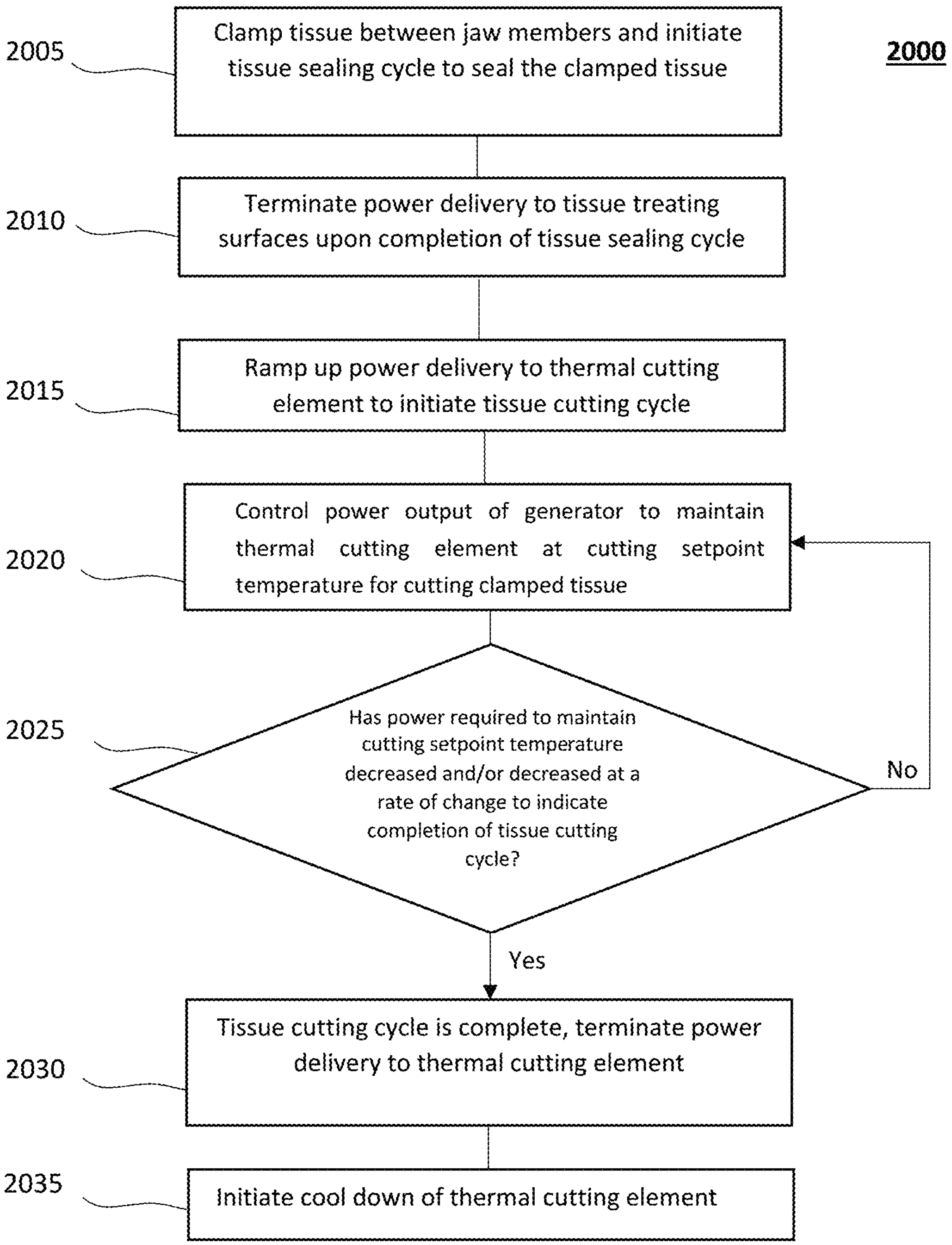
FIG. 9 is a flow chart showing a method for performing a closed jaws tissue seal/cut procedure in accordance with the present disclosure.

FIG. 9 is a flow chart showing the various steps associated with a method 2000 for detecting the completion of a closed jaws tissue sealing/cutting cycle. As an initial step 2005, the jaw members, e.g., jaw members 110, 120, are disposed in the approximated position and clamped on tissue and switch 80 is activated to deliver power from the generator "G" to tissue treating surfaces 114, 124 to seal the clamped tissue. As described above with respect to FIG. 7, a determination that jaw members 110, 120 are in the approximated position and clamped on tissue may be determined based on the state of one or both of a jaw aperture sensor and a jaw force sensor. In step 2010, power delivery from the generator "G" to tissue treating surfaces 114, 124 is terminated upon completion of the tissue sealing cycle. In step 2015, the tissue cutting cycle is initiated as power delivery from the generator "G" to the thermal cutting element 130 is ramped up to increase the temperature of the thermal cutting element 130 to a cutting setpoint temperature suitable for cutting sealed tissue (e.g., between about 350° C. and about 550° C.). In step 2020, the generator "G" controls power delivery to the thermal cutting element 130 to maintain the thermal cutting element 130 at the cutting setpoint temperature to cut the sealed tissue. In step 2025, it is determined if the power output of the generator "G" required to maintain the thermal cutting element 130 at its cutting setpoint temperature to cut tissue has decreased, decreased at a rate of change that exceeds a pre-determined rate of change threshold, and/or fallen below a power threshold value (as discussed above). If the power output of the generator "G" required to maintain the thermal cutting element 130 at its cutting setpoint temperature to cut tissue has not met the condition(s) of step 2025, the method 2000 returns to step 2020. If the power output of the generator "G" required to maintain the thermal cutting element 130 at its cutting setpoint temperature has met the condition(s) of step 2025, the tissue cutting cycle is determined to be complete and the generator "G" terminates power delivery in step 2030. In step 2035, the cool down of thermal cutting element 130 is initiated and the temperature of the thermal cutting element 130 and/or the jaw members 110, 120 decreases over time.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. An electrosurgical system, comprising:

an electrosurgical device including:

first and second jaw members each defining a tissue treating surface, the first and second jaw members pivotably coupled to one another such that at least one of the first or second jaw members is movable relative to the other from a spaced-apart position to an approximated position to grasp tissue between the tissue treating surfaces; and a thermal cutting element coupled to the first jaw member and configured to cut tissue in contact with the thermal cutting element, the thermal cutting element separate from and protruding beyond the tissue treating surface of the first jaw member toward the second jaw member; and an electrosurgical generator configured to deliver power to the tissue treating surfaces for sealing tissue grasped between the tissue treating surfaces and to deliver power directly to the thermal cutting element via at least one conductive trace disposed within the thermal cutting element for heating the thermal cutting element via resistive heating and cutting tissue in contact with the thermal cutting element, the at least one conductive trace electrically coupling the thermal cutting element to the electrosurgical generator, wherein:

when the jaw members are in the approximated position, the electrosurgical generator is configured to deliver power to the thermal cutting element to maintain a temperature of the thermal cutting element at an operating temperature for cutting the sealed tissue grasped between the tissue treating surfaces; and when the jaw members are in the spaced-apart position, the electrosurgical generator is configured to:

terminate delivery of power to the tissue treating surfaces;

deliver power to the thermal cutting element to warm the thermal cutting element to a standby setpoint temperature;

deliver power to the thermal cutting element to maintain the temperature of the thermal cutting element at the standby setpoint temperature;

deliver power to the thermal cutting element to increase the temperature of the thermal cutting element from the standby setpoint temperature to a cutting setpoint temperature in response to a determination of contact between tissue and the thermal cutting element; and control delivery of power to perform open jaws tissue dissection, wherein the control of power delivery maintains the temperature of the thermal cutting element at the cutting setpoint temperature to dissect tissue in contact with the thermal cutting element without delivery of power to the tissue treating surfaces.

2. The electrosurgical system according to claim 1, wherein the cutting setpoint temperature is between about 350° C. and about 550° C.

3. The electrosurgical system according to claim 1, wherein the standby setpoint temperature is between about 20° C. and about 60° C.

4. The electrosurgical system according to claim 1, wherein the determination of contact between tissue and the thermal cutting element is based on the power delivered to the thermal cutting element to maintain the thermal cutting element at the standby setpoint temperature exceeding a threshold power level.

5. The electrosurgical system according to claim 4, wherein the electrosurgical generator is configured to deliver power to the thermal cutting element to decrease the temperature of the thermal cutting element from the cutting setpoint temperature to the standby setpoint temperature in response to a determination that the thermal cutting element is not in contact with tissue.

6. The electrosurgical system according to claim 5, wherein the determination that the thermal cutting element is not in contact with tissue is based on the power delivered to the thermal cutting element to maintain the thermal cutting element at the cutting setpoint temperature decreasing to a level below a threshold power level.

7. The electrosurgical system according to claim 1, wherein completion of cutting of the tissue grasped between the tissue treating surfaces is determined based on a decrease of the power delivered to the thermal cutting element to maintain the temperature of the thermal cutting element at the operating temperature.

8. The electrosurgical system according to claim 1, wherein the electrosurgical generator, when the jaw members are in the approximated position, is configured to:

deliver power to the tissue treating surfaces for sealing tissue grasped between the tissue treating surfaces; and deliver power to the thermal cutting element while delivery of power to the tissue treating surfaces is terminated for cutting the sealed tissue grasped between the tissue treating surfaces.

9. The electrosurgical system according to claim 1, wherein the thermal cutting element is at least partially located in a longitudinally extending slot, wherein the thermal cutting element includes an upper surface, and wherein the upper surface protrudes beyond the slot and the first treating surface towards the second treating surface.

10. The electrosurgical system according to claim 1, wherein the thermal cutting element includes a base substrate having an upper surface that extends beyond the first treating surface towards the second treating surface, wherein the upper surface is coupled to at least two sides, and wherein an insulating layer is on at least one side of at least two sides of the base substrate, and wherein the conductive trace is on the insulated layer on the at least one side.

11. An electrosurgical system, comprising:

an electrosurgical device including first and second jaw members each defining a tissue treating surface, the first and second jaw members pivotably coupled to one another such that at least one of the first or second jaw members is movable relative to the other from a spaced-apart position to an approximated position to grasp tissue between the tissue treating surfaces, the first jaw member including a thermal cutting element configured to cut tissue in contact with the thermal cutting element, the thermal cutting element separate from and protruding beyond the tissue treating surface of the first jaw member toward the second jaw member; and an electrosurgical generator electrically coupled to the first and second jaw members and configured to:

deliver power to the tissue treating surfaces to seal tissue grasped between the tissue treating surfaces when the jaw members are in the approximated position;

deliver power to at least one conductive trace disposed within the thermal cutting element to heat the thermal cutting element via resistive heating to maintain a temperature of the thermal cutting element at an operating temperature for cutting sealed tissue in contact with the thermal cutting element and grasped between the tissue treating surfaces when the jaw members are in the approximated position, the at least one conductive trace electrically coupling the thermal cutting element to the electrosurgical generator;

terminate delivery of power to the tissue treating surfaces when the jaw members are in the spaced apart position;

deliver power to the thermal cutting element when the jaw members are in the spaced apart position to warm the thermal cutting element to a standby setpoint temperature;

control delivery of power to the thermal cutting element to maintain the temperature of the thermal cutting element at the standby setpoint temperature when the jaw members are in the spaced apart position;

control delivery of power to the thermal cutting element to increase the temperature of the thermal cutting element from the standby setpoint temperature to a cutting setpoint temperature to perform open jaws tissue dissection in response to a determination of contact between tissue and the thermal cutting element;

control delivery of power to the thermal cutting element to maintain the temperature of the thermal cutting element at the cutting setpoint temperature to dissect tissue in contact with the thermal cutting element while delivery of power to the tissue treating surfaces is terminated when the jaw members are in the spaced apart position; and terminate delivery of power to the thermal cutting element to decrease the temperature of the thermal cutting element.

12. The electrosurgical system according to claim 11, wherein the operating temperature of the thermal cutting element for cutting sealed tissue grasped between the tissue treating surfaces is between about 350° C. and about 550° C.

13. The electrosurgical system according to claim 11, wherein the cutting setpoint temperature of the thermal cutting element for dissecting tissue when the jaw members are in the spaced apart position is between about 350° C. and about 550° C.

14. The electrosurgical system according to claim 11, wherein the standby setpoint temperature of the thermal cutting element when the jaw members are in the spaced apart position is between about 20° C. and about 60° C.

15. The electrosurgical system according to claim 11, wherein the determination of contact between tissue and the thermal cutting element is based on the power delivered to the thermal cutting element to maintain the thermal cutting element at the standby setpoint temperature exceeding a threshold power level.

16. The electrosurgical system according to claim 15, wherein the electrosurgical generator is configured to control delivery of power to the thermal cutting element to decrease the temperature of the thermal cutting element from the cutting setpoint temperature to the standby setpoint temperature in response to a determination that the thermal cutting element is not in contact with tissue.

17. The electrosurgical system according to claim 16, wherein the determination that the thermal cutting element is not in contact with tissue is based on the power delivered to the thermal cutting element to maintain the thermal cutting element at the cutting setpoint temperature decreasing to a level below a threshold power level.

18. The electrosurgical system according to claim 11, wherein completion of cutting of the tissue grasped between the tissue treating surfaces is determined based on a decrease of the power delivered to the thermal cutting element to maintain the temperature of the thermal cutting element at the operating temperature.

19. The electrosurgical system according to claim 11, wherein the electrosurgical generator, when the jaw members are in the approximated position, is configured to:

deliver power to the tissue treating surfaces for sealing tissue grasped between the tissue treating surfaces; and deliver power to the thermal cutting element while delivery of power to the tissue treating surfaces is terminated for cutting the sealed tissue grasped between the tissue treating surfaces.

20. An electrosurgical system, comprising:

an electrosurgical device including first and second jaw members each defining a tissue treating surface, the first and second jaw members pivotably coupled to one another such that at least one of the first or second jaw members is movable relative to the other from a spaced-apart position to an approximated position to grasp tissue between the tissue treating surfaces, the first jaw member including a thermal cutting element configured to cut tissue in contact with the thermal cutting element, the thermal cutting element separate from and protruding beyond the tissue treating surface of the first jaw member toward the second jaw member; and an electrosurgical generator electrically coupled to the first and second jaw members and configured to:

deliver power to the tissue treating surfaces to seal tissue grasped between the tissue treating surfaces when the jaw members are in the approximated position;

deliver power to the thermal cutting element via at least one conductive trace disposed within the thermal cutting element to heat the thermal cutting element via resistive heating to one of cut sealed tissue in contact with the thermal cutting element and grasped between the tissue treating surfaces when the jaw members are in the approximated position or dissect tissue determined to be in contact with the thermal cutting element when the jaw members are in the spaced apart position, the at least one conductive trace electrically coupling the thermal cutting element to the electrosurgical generator;

terminate delivery of power to the thermal cutting element upon detection of completion of the cutting of the sealed tissue when the jaw members are in the approximated position;

terminate delivery of power to the tissue treating surfaces when the jaw members are in the spaced apart position;

operate in a low-temperature standby mode to deliver power to the thermal cutting element to maintain the temperature of the thermal cutting element at a standby setpoint temperature between about 20° C. and about 60° C. when the jaw members are in the spaced apart position;

operate in a high-temperature cut mode to deliver power to the thermal cutting element in response to sensed contact between tissue and the thermal cutting element when the jaw members are in the spaced apart position to increase the temperature of the thermal cutting element from the standby setpoint temperature to a cutting setpoint temperature between about 350° C. and about 550° C. to perform open jaws tissue dissection;

control delivery of power to the thermal cutting element during operation in the high-temperature cut mode to maintain the temperature of the thermal cutting element at the cutting setpoint temperature for dissecting tissue in contact with the thermal cutting element while delivery of power to the tissue treating surfaces is terminated; and terminate delivery of power to the thermal cutting element to decrease the temperature of the thermal cutting element.

* * * * *